(12) United States Patent
Quintard et al.

(10) Patent No.: US 11,542,462 B2
(45) Date of Patent: Jan. 3, 2023

(54) METHOD FOR ACHIEVING MICROFLUIDIC PERFUSION OF A SPHEROID AND DEVICE SUITABLE FOR IMPLEMENTING SAID METHOD

(71) Applicant: Commissariat à l'Energie Atomique et aux Energies Alternatives, Paris (FR)

(72) Inventors: Clément Quintard, Grenoble (FR); Jean-Luc Achard, Grenoble (FR); Yves Fouillet, Grenoble (FR)

(73) Assignee: Commissariat à l'Energie Atomique et aux Energies Alternatives, Paris (FR)

( * ) Notice: Subject to any disclaimer, the term of this patent is extended or adjusted under 35 U.S.C. 154(b) by 15 days.

(21) Appl. No.: 17/194,948

(22) Filed: Mar. 8, 2021

(65) Prior Publication Data

US 2021/0277349 A1    Sep. 9, 2021

(30) Foreign Application Priority Data

Mar. 9, 2020    (FR) ..................................... 20 02290

(51) Int. Cl.
*C12M 1/00* (2006.01)
*B01L 3/00* (2006.01)
(Continued)

(52) U.S. Cl.
CPC ....... *C12M 29/10* (2013.01); *B01L 3/502761* (2013.01); *C12M 23/16* (2013.01);
(Continued)

(58) Field of Classification Search
CPC ...... C12M 29/10; C12M 23/16; C12M 23/22; C12M 25/14; B01L 3/502761;
(Continued)

(56) References Cited

U.S. PATENT DOCUMENTS

2016/0097028 A1    4/2016    Tung et al.
2020/0224137 A1    7/2020    Kumacheva et al.

FOREIGN PATENT DOCUMENTS

JP    2012-75391 A    4/2012
WO    WO 2019/010587 A1    1/2019
WO    WO 2019/183998 A1    10/2019

OTHER PUBLICATIONS

French Preliminary Search Report dated Nov. 10, 2020 in French Application 20 02290 filed Mar. 9, 2020 (with English Translation of Categories of Cited Documents and Written Opinion), 9 pages.

*Primary Examiner* — Jennifer Wecker
*Assistant Examiner* — Oyeleye Alexander Alabi
(74) *Attorney, Agent, or Firm* — Oblon, McClelland, Maier & Neustadt, L.L.P.

(57) ABSTRACT

A method for achieving microfluidic perfusion of a spheroid, the method being implemented in a microfluidic device that includes a cavity for hydrodynamically trapping the spheroid, the method including performing a first injection of a gel containing the spheroid into the microfluidic network, hydrodynamically trapping the spheroid in the trapping cavity of the microfluidic network, performing a second injection of a fluid that is non-miscible with the gel into the microfluidic network with a view to flushing away gel present in the network, except in the trapping cavity, crosslinking the gel present around the spheroid, in the trapping cavity, performing a third injection of a culture medium into the microfluidic network with a view to perfusing the spheroid petrified in its gelled environment, and located in the trapping cavity.

14 Claims, 8 Drawing Sheets

(51) Int. Cl.
*C12M 3/06* (2006.01)
*G01N 33/483* (2006.01)

(52) U.S. Cl.
CPC ......... *C12M 23/22* (2013.01); *G01N 33/4833* (2013.01); *B01L 2300/0864* (2013.01); *B01L 2300/0883* (2013.01); *B01L 2400/0475* (2013.01)

(58) Field of Classification Search
CPC ..... B01L 2300/0864; B01L 2300/0883; B01L 2400/0475; G01N 33/4833
See application file for complete search history.

US 11,542,462 B2

METHOD FOR ACHIEVING MICROFLUIDIC PERFUSION OF A SPHEROID AND DEVICE SUITABLE FOR IMPLEMENTING SAID METHOD

TECHNICAL FIELD OF THE INVENTION

The present invention relates to a method for achieving microfluidic perfusion of a spheroid.

The invention also relates to a microfluidic device configured to implement said method.

PRIOR ART

The context of the invention is in the field of perfusion of cells, the objective of which is to provide three-dimensional cell-culture models that reproduce, as accurately as possible, by virtue of microfluidics, the in vivo environment of an organ.

Patent application WO2019/010587A1 (D1) mainly describes the creation of cell aggregates, in a device equipped with a plurality of microwells.

Solutions for culturing cell aggregates also exist. The aggregates generally take the form of spheroids. These solutions consist in trapping the spheroids in micro-wells, then in providing the nutrients required by the trapped spheroids and in monitoring the behavior of the spheroids in the culture. This is for example the case in patent applications Nos. US2016/304823A1, US2016/097028A1, US2014/227784A1 and US2013/217064A1. Patent application FR3079524A1 for its part describes one way of producing a microwell plate.

Patent application FR2452285 for its part relates to encapsulation of viable cells in a membrane.

Moreover, solutions for achieving microfluidic perfusion of spheroids also exist. Microfluidic perfusion enables long-term delivery of the nutrients required by the cells because it allows the culture medium to be continuously renewed, contrary to conventional well-based culture models.

With these microfluidic-perfusion solutions, a first approach consists in petrifying the spheroid in a gel and perfusing it via two side channels through which the culture medium flows. Such solutions are for example described in the following publications:

Nashimoto, Y., Hayashi, T, Kunita, I., Nakamasu, A., Torisawa, Y. S., Nakayama, M., & Yokokawa, R. (2017). *Integrating perfusable vascular networks with a three-dimensional tissue in a microfluidic device. Integrative Biology*, 9(6), 506-518.

Van Duinen, V., Zhu, D., Ramakers, C., van Zonneveld, A. J., Vulto, P., & Hankemeier, T. (2019). *Perfused 3D angiogenic sprouting in a high-throughput in vitro platform. Angiogenesis*, 22(1), 157-165.

A second approach involves localizing the spheroid by virtue of a system for trapping hydrodynamically. The spheroid is injected through a fluidic inlet and is trapped in a location chosen by the designer of the microfluidic device. A continuous flow may then be applied to keep the spheroid under perfusion. Such solutions are for example described in the following publications:

Nourmohammadzadeh, M., Lo, J. F., Bochenek, M., Mendoza-Elias, J. E., Wang, Q., Li, Z. & Wang, Y. (2013). Microfluidic array with integrated oxygenation control for real-time live-cell imaging: effect of hypoxia on physiology of microencapsulated pancreatic islets. *Analytical chemistry*, 85(23), 11240-11249.

Ruppen, J., Cortes-Dericks, L., Marconi, E., Karoubi, G., Schmid, R. A., Peng, R. & Guenat, O. T. (2014). A microfluidic platform for chemoresistive testing of multicellular pleural cancer spheroids. *Lab on a Chip*, 14(6), 1198-1205.

These prior-art solutions for achieving microfluidic perfusion are however unsatisfactory for the following reasons:

they cannot be automated. The carrier gel of the spheroid is injected manually using a pipette and it is up to the operator to determine the moment at which he must stop the injection. This operation is tricky because it requires a compromise to be found between too slow an injection, which could result in the gel cross-linking before the central channel is completely filled, and too rapid an injection, which could result in the gel overflowing into side channels;

if the spheroid is not encapsulated in a gel it bathes directly in the culture medium, this representing a poor reproduction of the physiological reality;

if the spheroid is encapsulated in a gel, the encapsulation must be carried out beforehand, this making it impossible to envision a continuous implementation that would limit human intervention;

in the latter case, the localization of the spheroid remains ephemeral and subject to fluctuations in the flow, this making it impossible to envision vascularization of the spheroid.

The aim of the invention is to provide a method for achieving microfluidic perfusion of a spheroid that allows one or more of the drawbacks of the prior-art solutions to be resolved. The proposed method notably:

allows the physiological reality of the living being from which the cells were sampled to be reproduced as accurately as possible;

allows human interventions to be limited, so as to allow perfect reproducibility over time to be achieved; and is able to be implemented automatically.

DESCRIPTION OF THE INVENTION

This aim is achieved via a method for achieving microfluidic perfusion of a spheroid, said method being implemented in a microfluidic device that comprises:

a main microfluidic circuit connected between said microfluidic inlet point and said microfluidic outlet point, the main microfluidic circuit comprising at least one central channel comprising a constriction forming a cavity for trapping hydrodynamically, a secondary microfluidic circuit connected to the main microfluidic circuit, in parallel to said constriction, said constriction being configured so that its resultant cross-sectional area after blockage by said spheroid induces a head loss through said central channel that is larger than the head loss present in the secondary microfluidic circuit.

Said method comprising the following steps:

performing a first injection of a gel containing said spheroid into the microfluidic network, hydrodynamically trapping said spheroid in the trapping cavity of the microfluidic network, performing a second injection of a fluid that is non-miscible with said gel into said microfluidic network with a view to flushing away gel present in the network, except in the trapping cavity, cross-linking the gel present around the spheroid, in the trapping cavity, performing a third injection of a culture medium into said microfluidic network with a view to perfusing the spheroid petrified in its gelled environment, and located in the trapping cavity.

According to one particularity, the fluid that is non-miscible with the gel is air.

According to another particularity, the gel is composed of a mixture of fibrinogen and thrombin, of a mixture of fibrinogen, collagen and thrombin, of pure collagen or of a synthetic hydrogel.

According to another particularity, each step of performing an injection is carried out using positive and/or negative pressure.

According to one variant embodiment, the method comprises a step of adding endothelial cells to the gel with a view to achieving a vascularization of the spheroid.

According to one variant embodiment, the method comprises a step of adding endothelial cells to the culture medium with a view to achieving a vascularization of the spheroid.

The invention also relates to the microfluidic device for achieving perfusion of a spheroid intended to implement the method such as defined above, said device comprising:
  a microfluidic inlet, a microfluidic outlet and means for injecting fluid through said microfluidic inlet,
  at least one microfluidic unit that comprises:
    a microfluidic inlet point connected to said microfluidic inlet and a microfluidic outlet point connected to said microfluidic outlet,
    a main microfluidic circuit connected between said microfluidic inlet point and said microfluidic outlet point, the main microfluidic circuit comprising at least one central channel comprising a constriction forming said cavity for trapping hydrodynamically,
    a secondary microfluidic circuit connected to the main microfluidic circuit, in parallel to said constriction,
    said constriction being configured so that its resultant cross-sectional area after blockage by said spheroid induces a head loss through said central channel that is larger than the head loss present in the secondary microfluidic circuit.

According to one particularity, the fluid-injecting means comprise:
  at least one reservoir containing a gel containing said spheroid,
  at least one reservoir containing a fluid that is non-miscible with said gel,
  at least one reservoir containing a culture medium.

According to another particularity, the fluid-injecting means comprise a unit for injecting using a positive pressure, which unit is connected to said microfluidic inlet, and/or a unit for injecting using a negative pressure, which unit is connected to said microfluidic outlet.

According to another particularity, the main microfluidic circuit and the secondary microfluidic circuit comprise microfluidic channels of rectangular cross section.

According to one particular embodiment, the device comprises a plurality of identical microfluidic units that are connected to one another to form a series, each microfluidic unit being identified by a rank i in the series, with i ranging from 1 to N and N being higher than or equal to 2, the microfluidic unit of rank i, for i ranging from 2 to N-1, having its microfluidic inlet connected to the microfluidic outlet of the microfluidic unit of rank i-1 and its microfluidic outlet connected to the microfluidic inlet of the microfluidic unit of rank i-1, the microfluidic unit of rank 1 having its microfluidic inlet point connected to said microfluidic inlet and the microfluidic unit of rank N having its microfluidic outlet point connected to said microfluidic outlet.

According to one particularity, the microfluidic units in series may be organized into a star or serpentine.

According to another particularity, the device comprises an auxiliary fluidic network for supplying and clearing and means for controlling the fluidic flow that are arranged in said auxiliary network and in each microfluidic unit.

BRIEF DESCRIPTION OF THE FIGURES

Other features and advantages will become apparent from the following detailed description, which is given with reference to the appended drawings, in which.

DETAILED DESCRIPTION OF AT LEAST ONE EMBODIMENT

The invention relates to a method for achieving microfluidic perfusion of a cell aggregate. Microfluidic perfusion enables long-term delivery of the nutrients required by the cells because it allows the culture medium to be continuously renewed.

By cell aggregate what is meant, according to the invention, is one or more types of cells that have self-assembled in three dimensions. Such a cell aggregate may notably be called a spheroid, an organoid, or a neurosphere. This aggregate may also be an islet of Langerhans. In the rest of the description, the generic term "spheroid" (referenced S) will be used to refer to such an aggregate, this term conventionally being employed in the field of the culture of living cells.

Nonlimitingly, such a spheroid S may for example have a diameter ranging from a few tens of µm to a few hundred µm.

All the steps of the method of the invention are implemented within the same integrally formed microfluidic component 1, which for example takes the form of a microfluidic chip. The microfluidic chip may have dimensions similar to those of a credit card.

Figure 1:
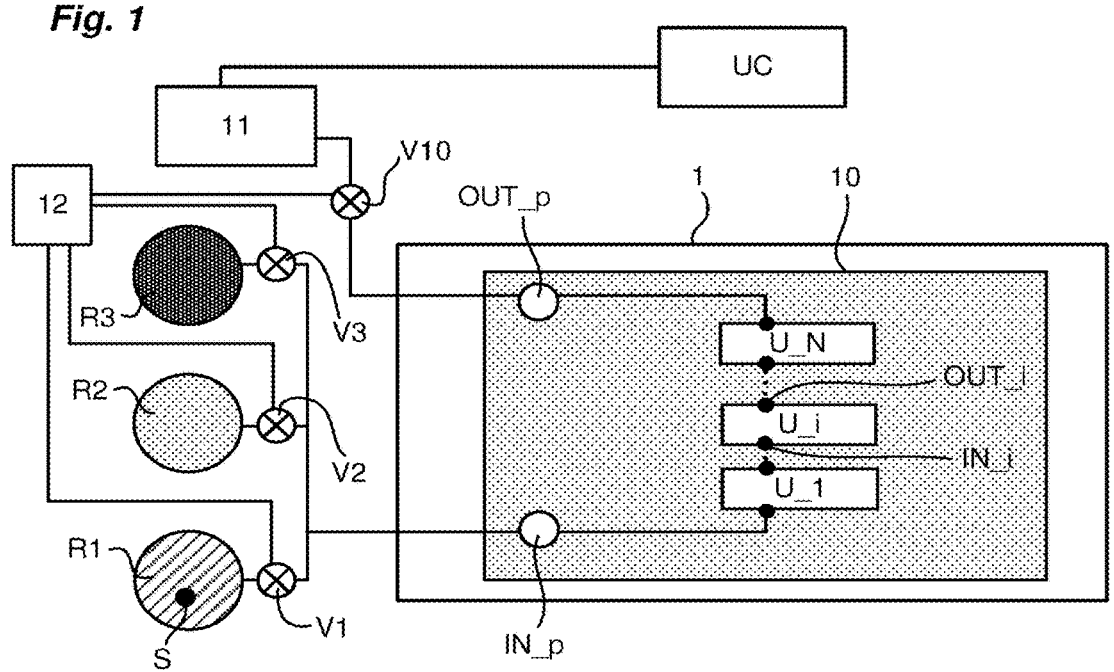
FIG. 1 schematically shows a first example of an embodiment of the device of the invention.

FIG. 1 thus shows a microfluidic device notably incorporating the microfluidic component.

The microfluidic component 1 comprises microfluidic connections and a microfluidic network 10.

The microfluidic connections comprise at least one microfluidic inlet IN_p and one microfluidic outlet OUT_p.

The microfluidic network 10 is composed of microfluidic channels, which are formed in the component, for example by machining, molding or another technical solution.

The dimensions of the microfluidic network 10 are chosen in light of the size of the studied biological objects, this size typically ranging from a few tens of microns to a few hundred microns. By way of example, the microfluidic channels are of square cross section and for example 400 μm in side length.

The microfluidic component 1 is incorporated into a microfluidic device.

The microfluidic device comprises means for injecting fluid into said microfluidic network 10 of the microfluidic component.

The fluid-injecting means may comprise a unit for injecting using positive pressure and/or a unit for injecting using negative pressure.

As shown in FIG. 1, the unit for injecting using negative pressure is connected to the microfluidic outlet OUT_p of the component 1, in order to allow an injection via suction into the interior of the microfluidic network 10 of the component 1.

The injecting means may comprise at least three fluidic reservoirs R1, R2, R3.

The fluidic reservoirs may be incorporated into the microfluidic component 1, for example in the form of cavities recessed into the component. As shown in FIG. 1, the reservoirs may also be external to said component, and connected to the microfluidic network of the component via a suitable fluidic connection.

Figure 2A:
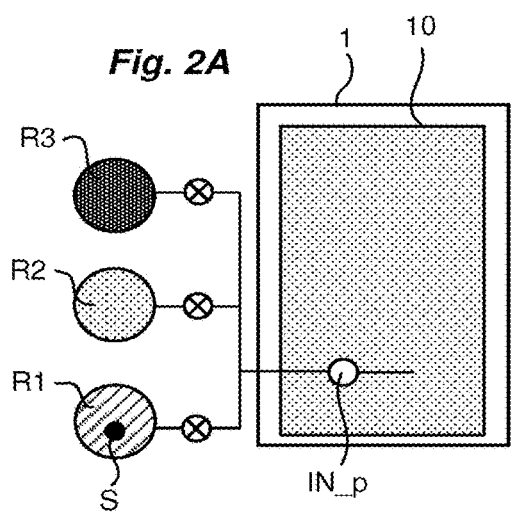
FIGS. 2A to 2C show three variant embodiments of the injecting means of the device of the invention.

As illustrated in FIG. 2A, the fluidic reservoirs R1, R2, R3, may be connected in parallel to a single microfluidic inlet IN_p of the microfluidic component 1.

Figure 2B:
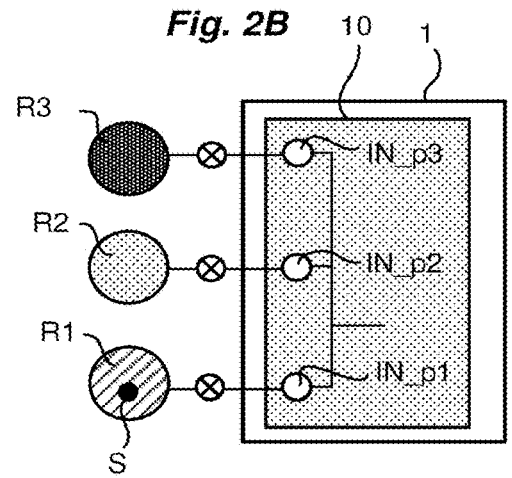

As illustrated in FIG. 2B, the fluidic reservoirs R1, R2, R3, may each be connected to one separate microfluidic inlet IN_p1, IN_p2, IN_p3 of the microfluidic component 1.

Figure 2C:
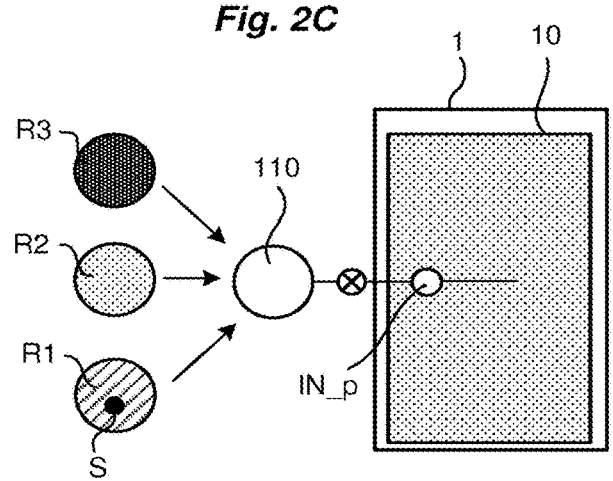

As illustrated by FIG. 2C, the injecting unit 11 may also comprise a single injecting module 110 connected to a single microfluidic inlet of the microfluidic component, said injecting module 110 being suitable for receiving, removably, each of the three reservoirs R1, R2, R3.

Nonlimitingly, the reservoir R1 may contain a gel in which the spheroid S is placed.

The gel may conventionally be composed of a mixture of fibrinogen and thrombin, or of a mixture of fibrinogen, collagen and thrombin, the interaction between the fibrinogen and the thrombin being used to cross-link the gel. The gel may also be composed of pure collagen, heat being used to cross-link it. The gel may also take the form of a synthetic hydrogel. A light source may then be used to cross-link it.

By way of example, the composition of the gel used may be the following: fibrinogen (6.6 mg/mL), aprotinin (0.15 TIU/mL), CaCl2 (2.5 mM), thrombin (1 IU/mL).

The gel may have a viscosity range comprised between that of water and a viscosity of several hundred times that of water (for example from 1 mPa·s to 1 Pa·s).

The amount of gel injected is typically of the order of the volume of the microfluidic network. By way of example, the injected gel volume may be 20 μL.

The reservoir R2 may contain a fluid that is immiscible with the gel. For example, it may be a question of a fluid such as air.

The reservoir R3 may contain a culture medium suitable for microfluidic perfusion of the spheroid.

The culture medium allows the nutrients required for the cells to develop correctly within the microfluidic device to be provided. It for example has a physiological pH of 7.4.

The fluid-injecting means may comprise a plurality of microfluidic valves Vx (with x identifying the valve—V1, V2, V3 and V10 in FIG. 1 by way of example) that are inserted into the microfluidic network 10 of the component 1 with a view to controlling the flows of fluid through this network 10 and at the outlet of each reservoir R1, R2, R3 with a view to controlling the fluid flow originating from each reservoir. Nonlimitingly, these valves Vx may be pneumatic valves. The fluid-injecting means may thus comprise a pneumatic actuating system 12 allowing each valve Vx to be actuated individually. Each valve Vx may be in the open state, in which it permits the flow of fluid, or in the closed state, in which it blocks the flow of fluid. Each valve Vx may also be controlled in an intermediate state with a view to controlling the fluid flow through the channel in which it is inserted.

Nonlimitingly, the valves may be produced using a hyperelastic membrane incorporated into the component. Subjected to a positive or negative pressure, such a membrane is made to deform in a cavity or in a channel with a view to controlling fluid flow. Such valve solutions are described in patent applications EP3326717A1 and EP3085444A1.

The fluid-injecting means may comprise a control unit UC. Such a control unit UC may notably comprise a programmable logic controller tasked with executing commands intended for each injecting unit 11 and for said pneumatic actuating system 12, with a view to implementing the steps of the method of the invention. The use of a control unit UC in the device allows the implementation of the method to be entirely automated. The control unit runs the instructions and sends successive commands to the various means of the device, notably with a view to controlling the fluid flows through the component 1.

The microfluidic component 1 comprises one or more microfluidic units U_i arranged between its microfluidic inlet IN_p and its microfluidic outlet OUT_p. When the component comprises a plurality of units, the latter are each intended to trap one separate spheroid and to allow its spheroid to be perfused.

Figure 3A:
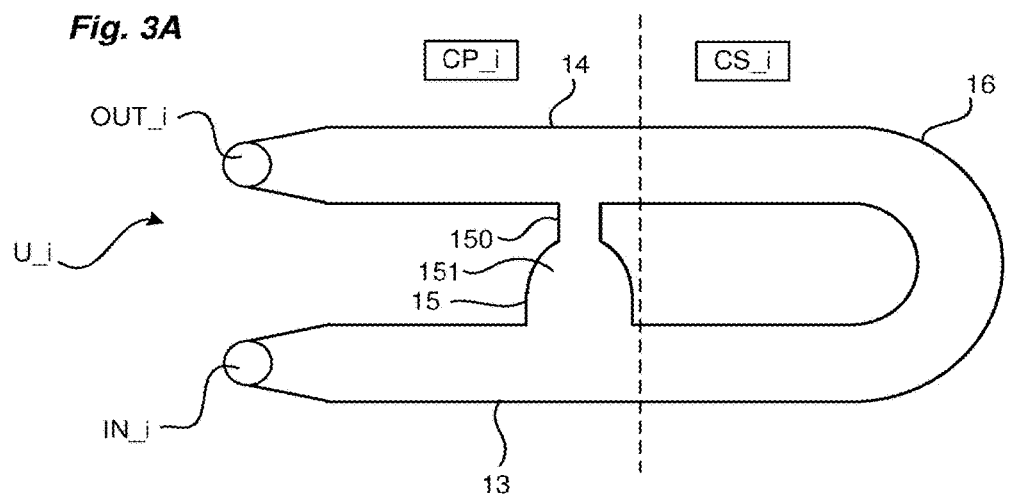
FIG. 3A shows a microfluidic unit employed in the microfluidic component of the device of the invention.

With reference to FIG. 3A, each microfluidic unit U_i comprises a microfluidic inlet point IN_i and a microfluidic outlet point OUT_i.

Between its microfluidic inlet point IN_i and its microfluidic outlet point OUT_i, each microfluidic unit U_i comprises a main microfluidic circuit CP_i comprising two side channels 13, 14 and a central channel 15 connecting the two side channels 13, 14.

Figure 3B:
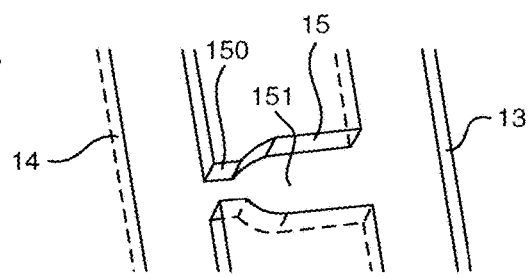
FIG. 3B shows the hydrodynamic trap via a view in three dimensions.

The central channel 15 of the main microfluidic circuit CP_i comprises a constriction 150 or restriction forming a cavity 151 for dynamically trapping a spheroid. FIG. 3B shows an exemplary embodiment of the constriction 150 and therefore of the formed cavity 151.

The microfluidic unit U_i also comprises a secondary microfluidic circuit CS_i comprising a secondary channel 16 connected to the main microfluidic circuit CP_i, in parallel to its central channel 15, so as to form a bypass with respect to its constriction 115. In FIG. 3A, the two circuits have been separated by a dashed line.

According to the invention, the constriction 150 is configured so that its resultant cross-sectional area after blockage by the spheroid S induces a larger head loss through the central channel 15 than the head loss present in the secondary microfluidic circuit CS_i. More precisely, the hydraulic resistances of the central channel 15 and of the secondary microfluidic circuit CS_i, which resistances are denoted $R_p$ and $R_s$, respectively, are, before the spheroid has been trapped, such that $R_p < R_s$ and, after the spheroid has been trapped, such that $R_p > R_s$. These inequalities guarantee the hydrodynamic operating principle of the trap. Of course, a plurality of configurations and a plurality of set-ups may be envisioned to meet these operating conditions.

The hydrodynamic trapping principle has notably been described in the following publication:

Tan, W. H., & Takeuchi, S. (2007). *A trap-and-release integrated microfluidic system for dynamic microarray applications. Proceedings of the National Academy of Sciences*, 104(4), 1146-1151.

Figure 4A:
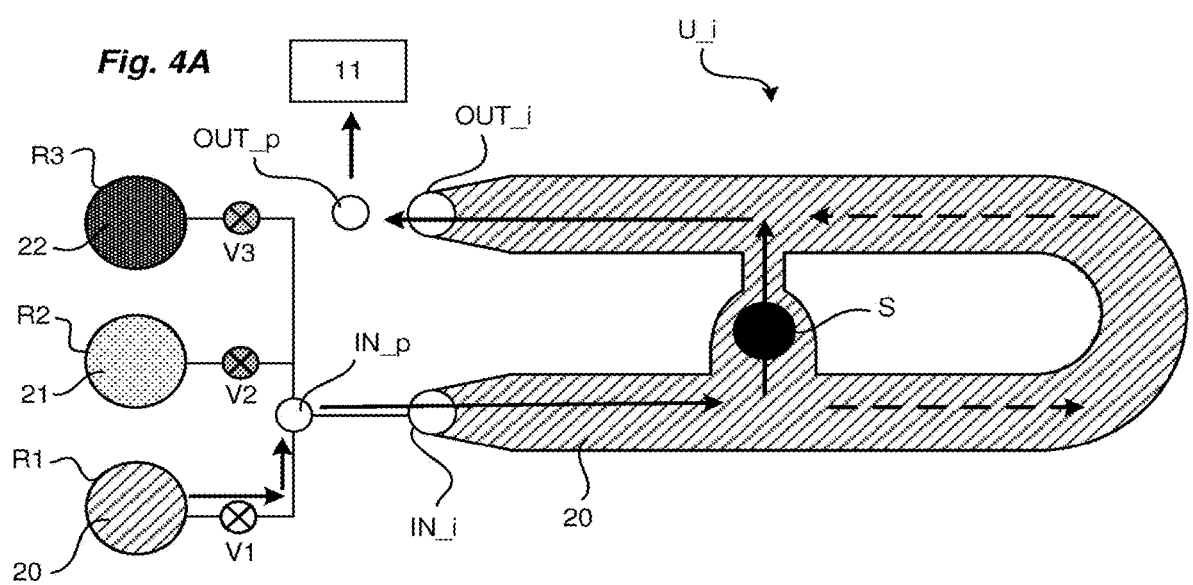
FIGS. 4A and 4B, 5A and 5B, and 6A and 6B illustrate the principle of the method of the invention applied to one microfluidic unit of the device.
Figure 4B:
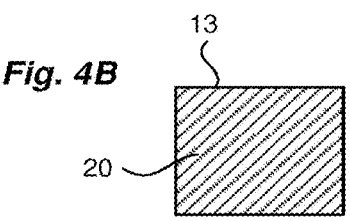
Figure 5A:
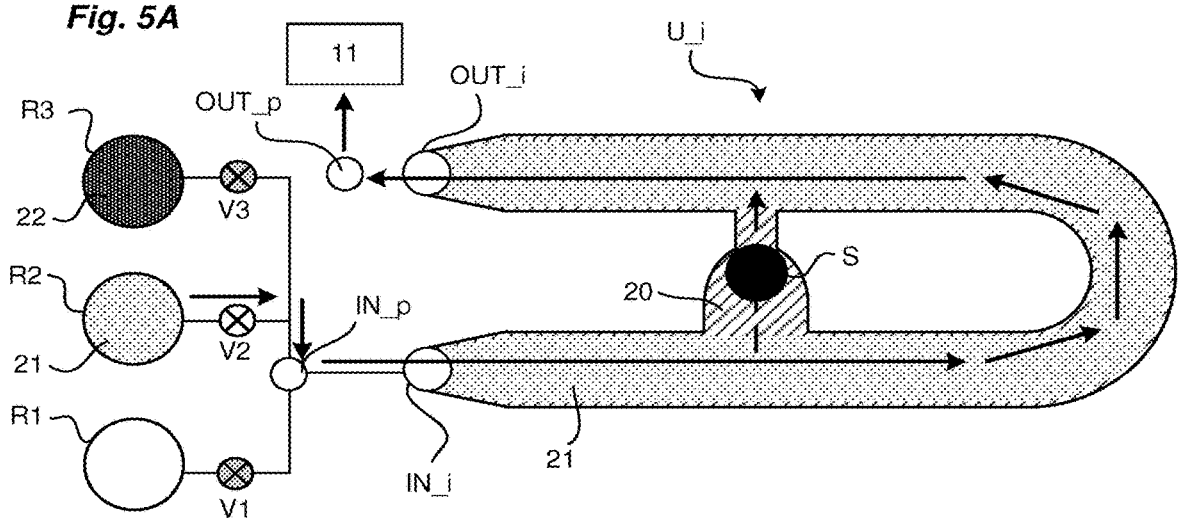
Figure 5B:
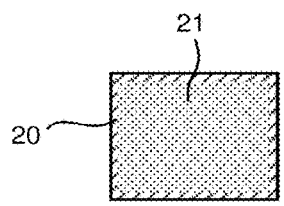
Figure 6A:
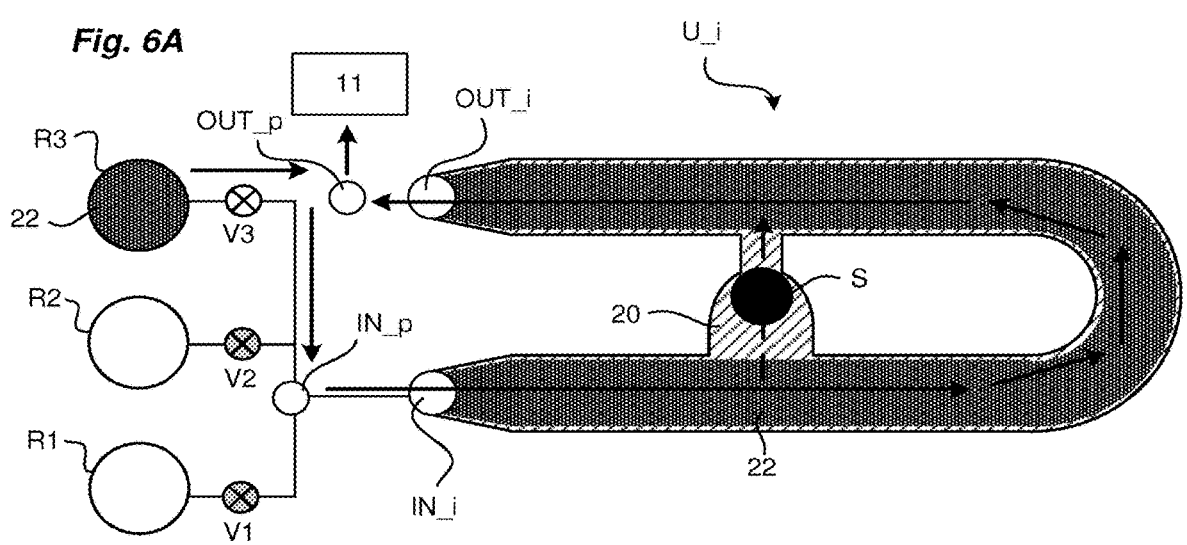
Figure 6B:
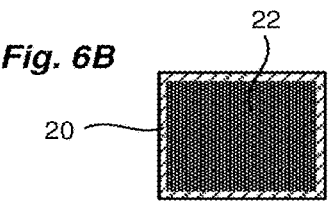

Nonlimitingly, with reference to FIGS. 4A and 4B with respect to its first phase, to FIGS. 5A and 5B with respect to its second phase and to FIGS. 6A and 6B with respect to its third phase, the method of the invention may be implemented using a device that has the following configuration:
- a single microfluidic unit (referenced U_i);
- three reservoirs R1, R2, R3 connected in parallel to a single microfluidic inlet IN_p of the microfluidic component;
- three separate valves V1, V2, V3 arranged at the outlet of each reservoir with a view to controlling the flow from the reservoir;
- a unit 11 for injecting using a negative pressure, this unit for example being composed of a syringe driver connected to the microfluidic outlet of the component.

FIGS. 4B, 5B and 6B are cross-sectional views of one of the two side channels 13, 14 of the main microfluidic circuit.

FIGS. 4A and 4B:

The valves V2 and V3 are closed and the valve V1 is open. The actuation of the injecting unit 11 using a negative pressure allows the gel 20 bearing the spheroid S present in the reservoir to be sucked into the microfluidic network 10.

During the injection, the gel 20 preferentially flows (solid arrows) through the main microfluidic circuit CP_i entraining the spheroid S into the constriction 150.

At the end of the injection, the spheroid S blocks the constriction 150 and is lodged in the cavity 151, allowing the component 1 to adopt the hydrodynamic situation described above in which the resultant cross-sectional area in the constriction 150, after blockage by the spheroid S, induces a larger head loss through the central channel 15 of the main microfluidic circuit CP_i than the head loss present in the secondary microfluidic circuit CS_i. The flow is then mainly through the secondary microfluidic circuit CS_i, thus protecting the spheroid S from a high shear stress.

FIGS. 5A and 5B:

The valves V1 and V3 are closed and the valve V2 is open. The actuation of the unit 11 for injecting using a negative pressure allows the fluid that is immiscible with the gel to be injected into the network 10. This fluid may be air 21. The gel 20 present in the side channels 13, 14 of the main microfluidic circuit CP_i and present in the secondary channel 16 of the secondary microfluidic circuit CS_i is thus flushed away by the injection of air.

By capillary action, there however remains gel 20 on the walls of the side channels 13, 14 of the main microfluidic circuit CP_i and of the secondary channel 16 and in the cavity 151 around the spheroid S, thus engendering a gel/air interface along the microfluidic channels, this allowing the spheroid to be localized in the cavity 151, the spheroid then being secured in the gel 20. This interface is shown in cross section in FIG. 5B.

The gel 20 becomes cross-linked after a few minutes. The final configuration is suitable for a micro-fluidic perfusion of the spheroid S, which is secured in the gel 20, lodged in the cavity 151 and accessible to perfusion via the side channels 13, 14 of the main microfluidic circuit CP_i.

FIGS. 6A and 6B:

The last step may then be implemented by injecting the culture medium 22 into the microfluidic network 10. The valves V1 and V2 are closed and the valve V3 is open. The actuation of the unit 11 for injecting using a negative pressure allows the culture medium 22 to be injected into the network 10. The culture medium 22 present in the reservoir R3 is constantly oxygenated and is conventionally injected at a low flow rate for several days (the time over which the operator desires to culture the spheroid S).

Figure 7:
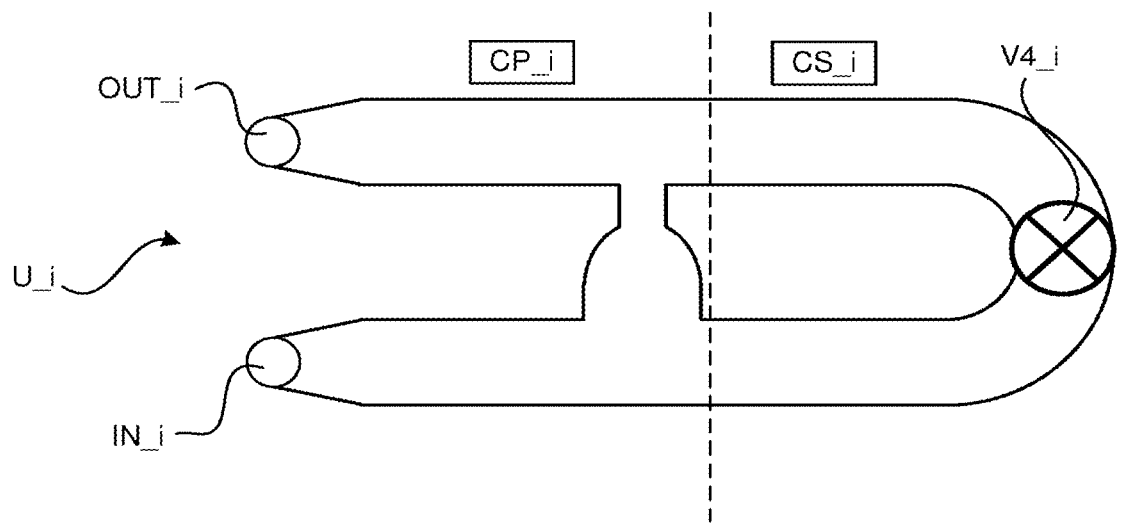
FIG. 7 shows another example of an embodiment of the microfluidic unit of the device of the invention.

With reference to FIG. 7, provision may be made for means for controlling the fluid flow through the spheroid S during the perfusion (third step above). More precisely, as the fluid may flow via the main microfluidic circuit CP_i and via the secondary microfluidic circuit CS_i, it may be desirable to control the flow through each of these two branches. This may be achieved by placing a valve V4 in the secondary microfluidic circuit CS_i. When the valve V4 is closed, the flow is then forced through the main microfluidic circuit CP_i, and therefore through the cavity 151 in which the gellified spheroid S is trapped. In any case, the arrangement of the device and the method of the invention allow the spheroid S trapped in the through-cavity 151 to be effectively perfused via the side channels 13, 14 and the central channel 15.

Advantageously, as indicated above, the device may comprise a plurality of microfluidic units U_i connected in series between the microfluidic inlet IN_p of the component and its microfluidic outlet OUT_p. The microfluidic units in series are for example all identical. The placement in series thus allows traps to be placed one after the other and thus a plurality of biological spheroids S to be studied within one and the same microfluidic component.

As indicated in FIG. 1, in a series, the microfluidic units may be identified by a rank i, with i ranging from 1 to N, N being higher than or equal to 2.

The microfluidic inlet point IN_1 of the microfluidic unit U_i of rank 1 is connected to the microfluidic inlet IN_p of the component 10.

The microfluidic outlet point OUT_N of the microfluidic unit U_N of rank N is connected to the microfluidic outlet OUT_p of the component.

As regards the microfluidic unit U_i of rank i, when i is comprised between 2 and N−1, its microfluidic inlet point IN_i is connected to the microfluidic outlet point OUT_i−1 of the unit U_i−1 of rank i−1 and its microfluidic outlet point OUT_i is connected to the microfluidic inlet point IN_i+1 of the unit U_i−1 of rank i+1.

Figure 8A:
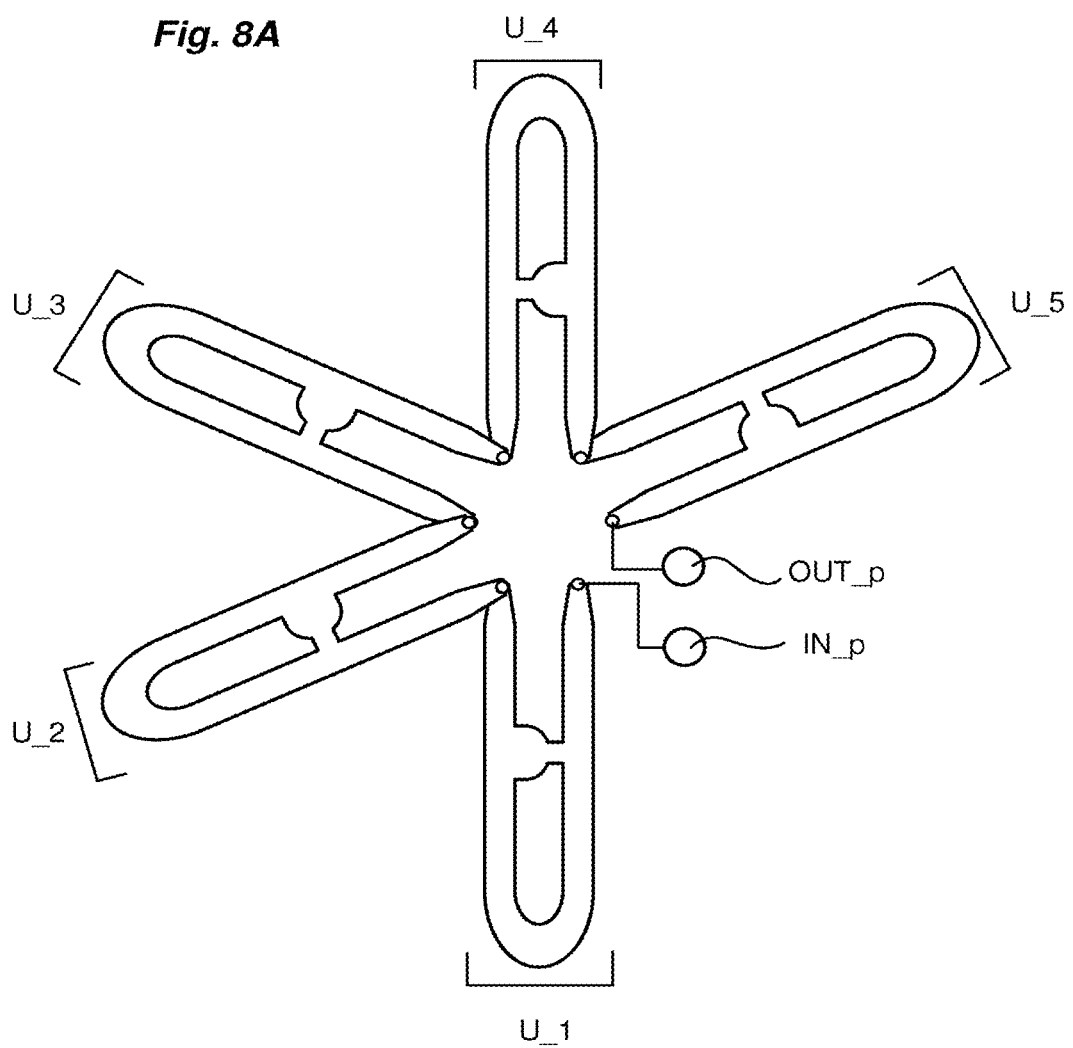
FIGS. 8A and 8B show two examples of placement in series of a plurality of microfluidic units.
Figure 8B:
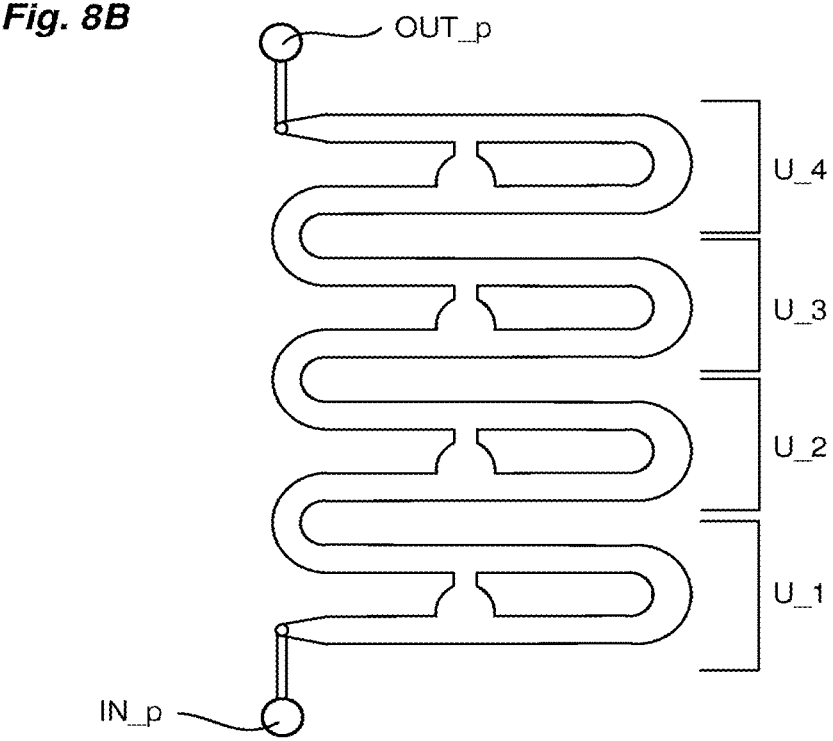

FIGS. 8A and 8B show two configurations of placement in series of a plurality of microfluidic units, according to the aforementioned principles.

In FIG. 8A, the microfluidic units are placed in series in a star configuration.

In FIG. 8B, the microfluidic units are placed in series in a serpentine configuration.

In these two configurations, the principle of the invention is applicable in an identical manner to that described above with respect to a single microfluidic unit (FIGS. 4A to 6B). Trapping the spheroid S in the cavity of the first unit U_1 of the series induces a large head loss, allowing a second spheroid to be conveyed to the cavity of the second microfluidic unit U_2 and so on up to the last microfluidic unit U_N of the series, thus allowing each microfluidic unit to receive in its cavity one separate spheroid.

Of course, it will be understood that other configurations of placement in series may absolutely be envisioned.

Subsequently, the other steps described above with respect to a single microfluidic unit apply in an identical manner to a plurality of units in series.

Figure 9:
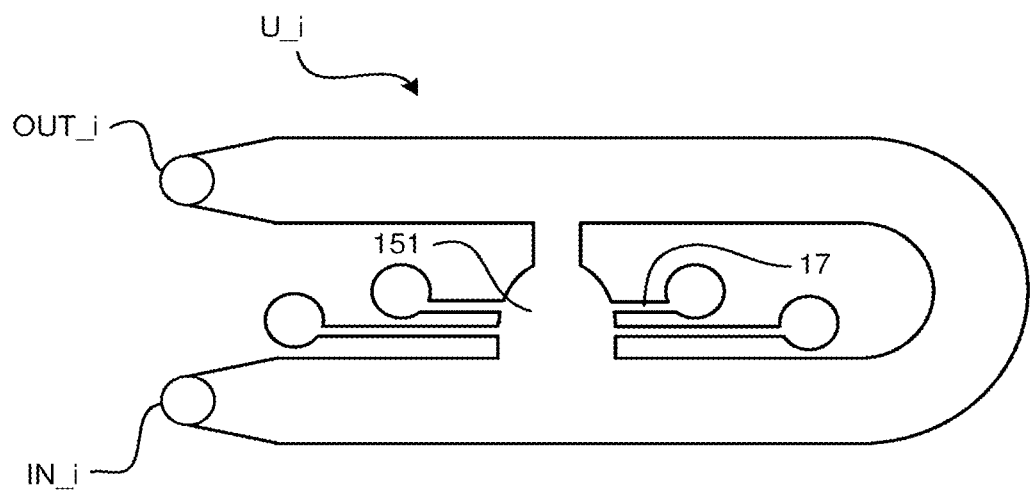
FIG. 9 shows another example of an embodiment of the microfluidic unit of the device of the invention.

FIG. 9 for its part illustrates the addition of a dual perfusing system to each microfluidic unit U_i. This system is composed of channels 17 that open directly into the cavity 151 in order to allow direct and independent perfusion of the spheroid S trapped in the cavity 151. This solution also allows a long-term perfusion to be carried out through the side channels 13, 14 of the microfluidic unit, then the spheroids to be perfused individually, without employing a valve-based system, and allows the secretions of the spheroid perfused by this auxiliary system to be analyzed.

Figure 10:
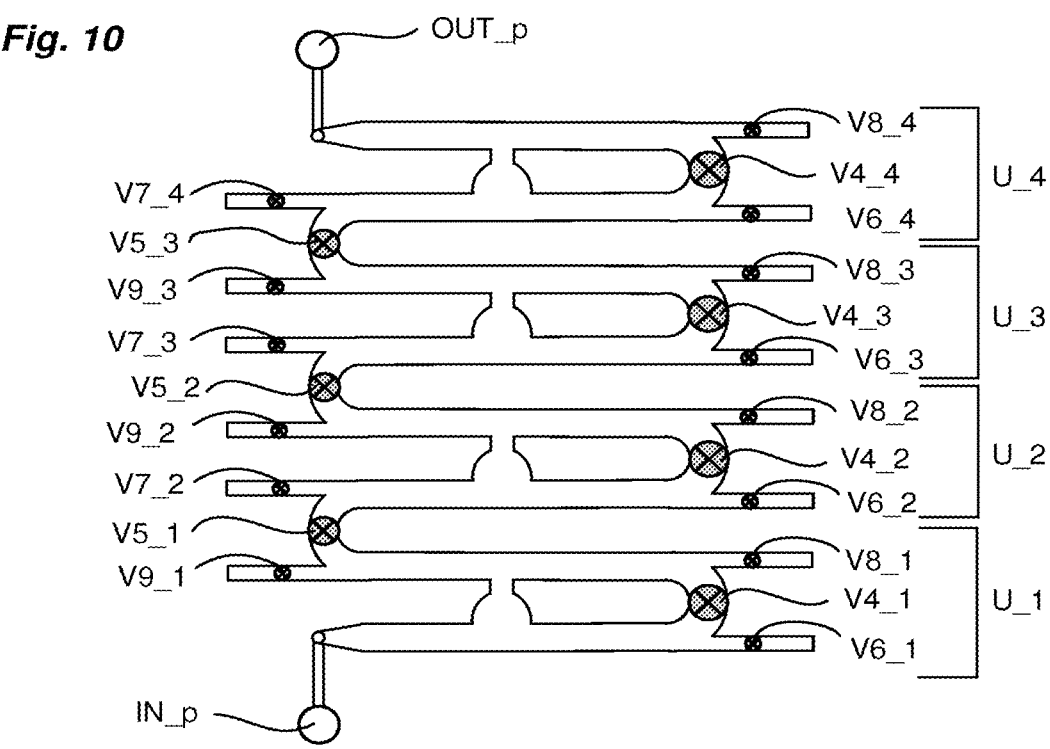
FIG. 10 shows placement in series of a plurality of microfluidic units in another variant embodiment.
Figure 11A:
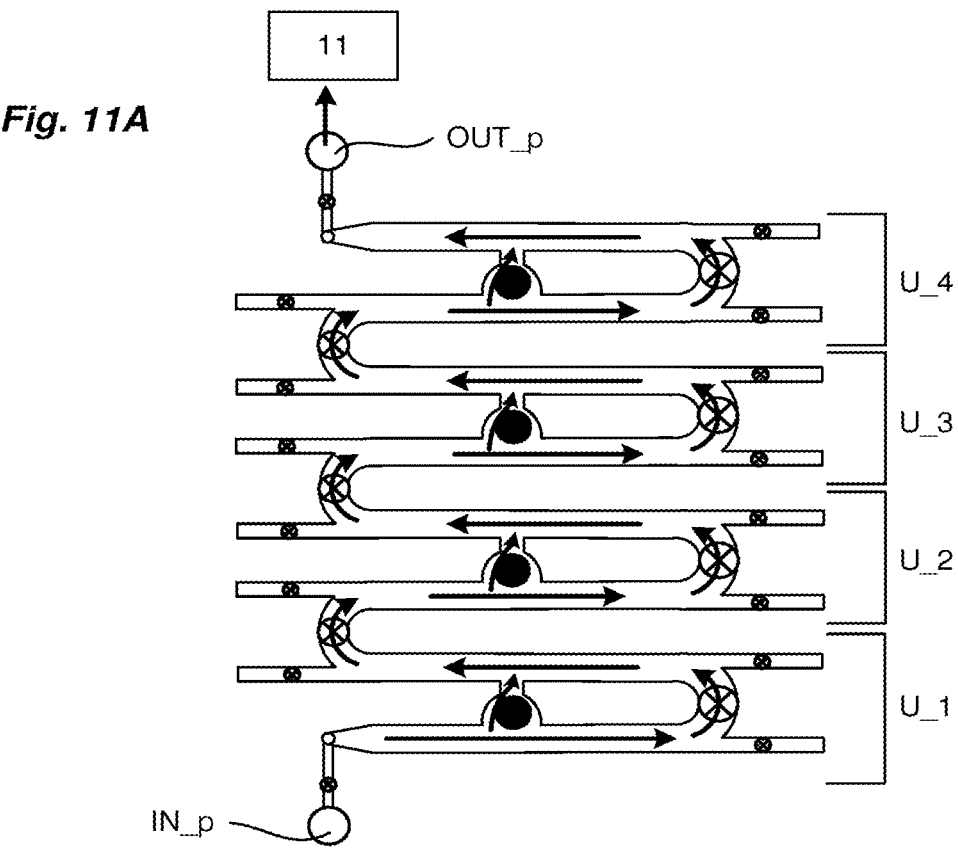
FIGS. 11A and 11B show two different possible operating modes of the solution shown in FIG. 10.
Figure 11B:
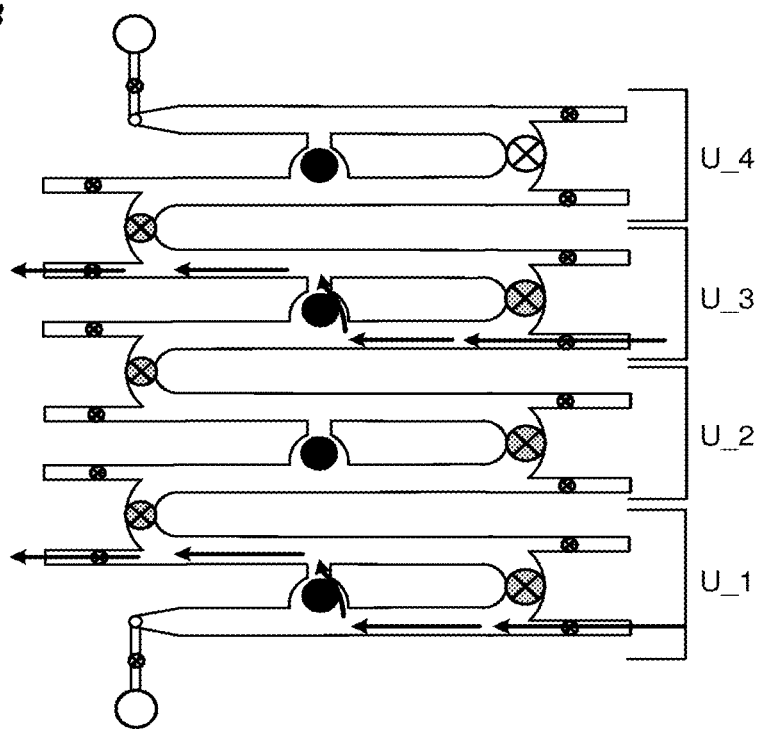

Furthermore, in a device comprising a plurality of microfluidic units placed in series, it may prove to be of relevance to study the spheroids individually. To do this, a routing system may also prove to be necessary, in order to be able to isolate each unit from the others, and to be able to convey the various liquids to outlet wells with a view to analyzing the secretions downstream. With this solution, in each unit of rank 2 to N–1, the side channels 13, 14 of the main microfluidic circuit CP_i may be extended at either end. Valves are also added in strategic locations. The localization of the spheroids and of their environment is achieved, as described above, through the main microfluidic circuit CP_i of each unit. Thus, in FIG. 10:

- valves V4_i are placed in the secondary microfluidic circuit CS_i of each unit U_i;
- valves V5_i are placed at the outlet of each microfluidic unit U_i;
- valves V6_i and V7_i are placed in the two extensions of the lateral channel 13 of each microfluidic unit U_i;
- valves V8_1 and V9_i are placed in the two extensions of the lateral channel 14 of each microfluidic unit U_i;

FIGS. 11A and 11B illustrate two embodiments of the device shown in FIG. 10.

FIG. 11A shows a conventional operating mode. Spheroids are trapped in each microfluidic unit U_i of the device. The valves V4_i and V5_i are opened in order to allow the perfusion of all of the spheroids, whereas the valves V6_i, V7_i, V8_i and V9_i remain closed.

In FIG. 11B, in the two microfluidic units U_1 and U3, the valves V6_1 and V9_1 and the valves V6_3 and V9_3 are opened, all the other valves remaining closed. In each of these two units U_1 and U_3, the flow is forced through the cavity 151 in which the relevant spheroid S is imprisoned, and the secretions of the spheroid S may then be analyzed downstream, on being collected via the extension of the channel 14. This principle may be replicated in order to analyze the individual secretions of each spheroid trapped in one separate microfluidic unit of the microfluidic device. In the example of FIG. 11B, the two other microfluidic units U_2 and U_4 are inactive.

Figure 12:
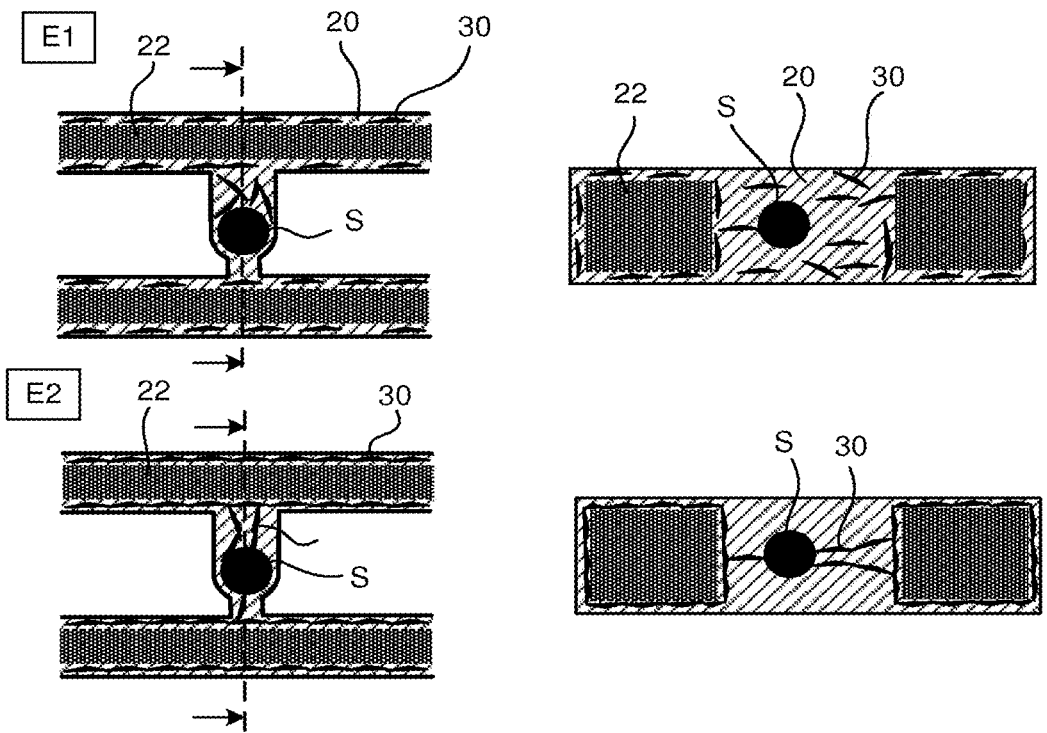
FIGS. 12 and 13 illustrate the implementation of a principle of vascularization of the spheroid, implemented using the device of the invention.
Figure 13:
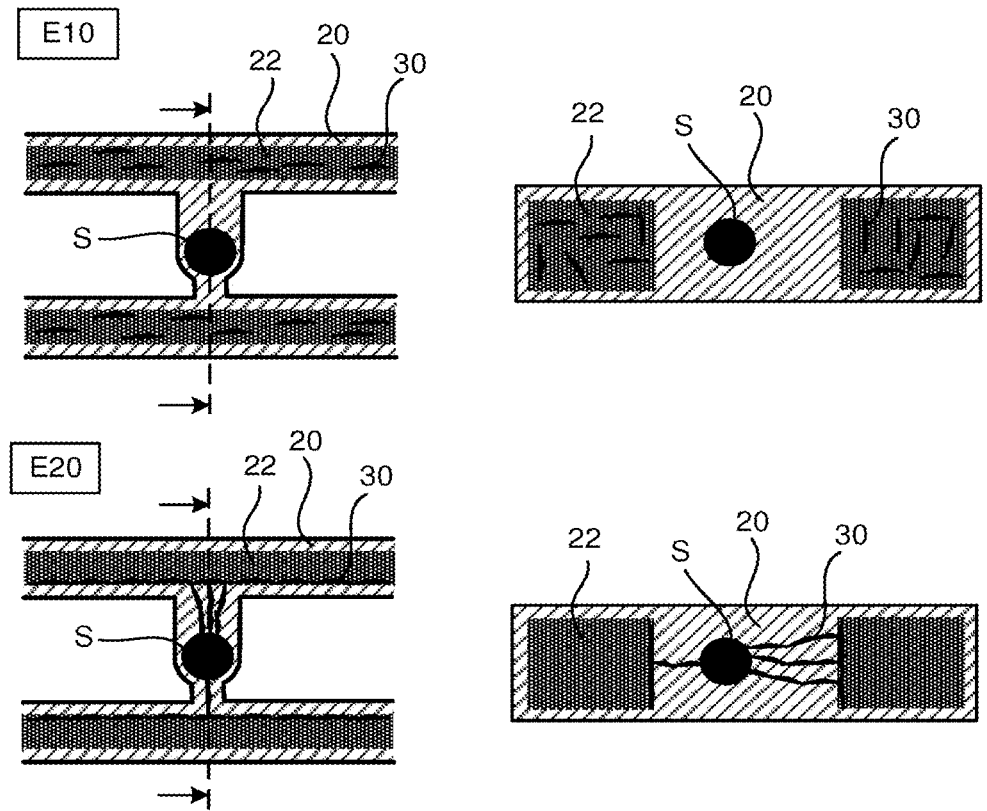

Moreover, with reference to FIGS. 12 and 13, the device of the invention may be employed to vascularize the spheroid S that has been trapped.

In FIG. 12, the spheroid S is vascularized by injecting endothelial cells 30 into the microfluidic network. The cells 30 may be suspended in the gel 20 beforehand (FIG. 12—E1, views from the side and in cross section along the dashed line). They then self-organize by vasculogenesis to create a vascular network within the gel 20 in order to perfuse the spheroid from either side (FIGS. 12—E2, views from the side and in cross section along the dashed line).

With reference to FIG. 13, another way of proceeding consists in suspending the endothelial cells 30 in the culture medium 22 (FIGS. 13—E10, views from the side and in cross section along the dashed line), then in stopping the flow and waiting a few minutes for the cells 30 to deposit on the desired walls (FIGS. 12—E20, views from the side and in cross section along the dashed line). The cells will then be able, by penetrating into the gel 20, to form a vascular network via angiogenesis and to perfuse the spheroid S.

In both cases, since a thin layer of gel is deposited on the walls of the microfluidic circuit, no surface coating is required to achieve a better adhesion of the cells. This solution thus has the advantage of rapidity.

It will be noted that the presence of a trapping through-cavity allows the spheroid to be better perfused, from either side, via a vascular network. Moreover, this vascular network is able to develop only if it benefits from a physical carrier, i.e. the hydrogel.

The solution of the invention thus has the following advantages:

- it is simple, easy and rapid to implement, notably by virtue of its automation;
- it is robust and reproducible, limiting manual interventions which are sources of errors;
- it requires little know-how, the control unit allowing the steps of the method to be executed in entirely automated manner;
- the principle of localizing the spheroid 4 and its environment 1 is based solely on physical principles (hydrodynamic trapping, effects of capillary action) and not on the skill of the operator. This solution is therefore easy to use, including by operators who are not experts.
- all the steps of the method are carried out within the same microfluidic component, the latter possibly being disposable and easily replaced in order to allow money to be made from the apparatus over time.

The invention claimed is:

1. A method for achieving microfluidic perfusion of a spheroid, said method being implemented in a microfluidic device that comprises:

a main microfluidic circuit (CP_i) connected between a microfluidic inlet point and a microfluidic outlet point, the main microfluidic circuit (CP_i) comprising at least one central channel comprising a constriction forming a cavity for trapping hydrodynamically, a secondary microfluidic circuit (CS_i) connected to the main microfluidic circuit (CP_i), in parallel to said constriction, said constriction being configured so that its resultant cross-sectional area after blockage by said spheroid induces a head loss through said central channel that is larger than the head loss present in the secondary microfluidic circuit (CS_i), wherein said method comprises the following steps:

performing a first injection of a gel containing said spheroid into the microfluidic network, hydrodynamically trapping said spheroid in the trapping cavity of the microfluidic network, performing a second injection of a fluid that is non-miscible with said gel into said microfluidic network with a view to flushing away gel present in the network, except in the trapping cavity, cross-linking the gel present around the spheroid, in the trapping cavity (151), performing a third injection of a culture medium into said microfluidic network with a view to perfusing the spheroid petrified in its gelled environment, and located in the trapping cavity.

2. The method as claimed in claim 1, wherein the fluid non-miscible with the gel is air.

3. The method as claimed in claim 1, wherein the gel is composed of a mixture of fibrinogen and thrombin, of a mixture of fibrinogen, collagen and thrombin, of pure collagen or of a synthetic hydrogel.

4. The method as claimed in claim 1, wherein each step of performing an injection is carried out using a positive and/or negative pressure.

5. The method as claimed in claim 1, futher comprising a step of adding endothelial cells to the gel with a view to achieving a vascularization of the spheroid.

6. The method as claimed in claim 1, further comprising a step of adding endothelial cells to the culture medium with a view to achieving a vascularization of the spheroid.

7. A microfluidic device for perfusing a spheroid intended to implement the method such as defined in claim 1, wherein said device comprises:
- a microfluidic inlet (IN_p), a microfluidic outlet (OUT_p) and means for injecting fluid through said microfluidic inlet (IN_p),
- at least one microfluidic unit (U_i) that comprises:
  - a microfluidic inlet point (IN_i) connected to said microfluidic inlet (IN_p) and a microfluidic outlet point (OUT_i) connected to said microfluidic outlet (OUT_p),
  - a main microfluidic circuit (CP_i) connected between said microfluidic inlet point and said microfluidic outlet point, the main microfluidic circuit (CP_i) comprising at least one central channel comprising a constriction forming said cavity (151) for trapping hydrodynamically,
  - a secondary microfluidic circuit (CS_i) connected to the main microfluidic circuit (CP_i), in parallel to said constriction,
  - said constriction being configured so that its resultant cross-sectional area after blockage by said spheroid induces a head loss through said central channel that is larger than the head loss present in the secondary microfluidic circuit (CS_i).

8. The device as claimed in claim 7, wherein the fluid-injecting means comprise:
- at least one reservoir (R1) containing a gel containing said spheroid,
- at least one reservoir (R2) containing a fluid that is non-miscible with said gel,
- at least one reservoir (R3) containing a culture medium.

9. The device as claimed in claim 7, wherein the fluid-injecting means comprise a unit for injecting using a positive pressure, which unit is connected to said microfluidic inlet (IN_p), and/or a unit for injecting using a negative pressure, which unit is connected to said microfluidic outlet (OUT_p).

10. The device as claimed in claim 7, wherein the main microfluidic circuit (CP_i) and the secondary microfluidic circuit (CS_i) comprise microfluidic channels of rectangular cross section.

11. The device as claimed in claim 7, further comprising a plurality of identical microfluidic units (U_i) that are connected to one another to form a series, each microfluidic unit (U_i) being identified by a rank i in the series, with i ranging from 1 to N and N being higher than or equal to 2, the microfluidic unit of rank i, for i ranging from 2 to N−1, having its microfluidic inlet connected to the microfluidic outlet of the microfluidic unit of rank i−1 and its microfluidic outlet connected to the microfluidic inlet of the microfluidic unit of rank i+1, the microfluidic unit of rank 1 having its microfluidic inlet point connected to said microfluidic inlet and the microfluidic unit of rank N having its microfluidic outlet point connected to said microfluidic outlet.

12. The device as claimed in claim 11, wherein the microfluidic units in series are organized into a star.

13. The device as claimed in claim 11, wherein the microfluidic units in series are organized into a serpentine.

14. The device as claimed in claim 7, further comprising an auxiliary fluidic network for supplying and clearing and means for controlling the fluidic flow that are arranged in said auxiliary network and in each microfluidic unit.

* * * * *